United States Patent
Stanek et al.

(10) Patent No.: US 6,858,743 B2
(45) Date of Patent: Feb. 22, 2005

(54) METHOD FOR THE PRODUCTION OF 2-COUMARONE AND SUBSTITUTED 2-COUMARONES

(75) Inventors: Michael Stanek, Linz (AT); Peter Hildebrand, Linz (AT); Curt Zimmermann, Riedmark (AT); Marianne Castelijns, Spaubeek (NL)

(73) Assignee: DSM Fine Chemicals Austria NFG GmbH & Co, KG, Linz (AT)

( * ) Notice: Subject to any disclaimer, the term of this patent is extended or adjusted under 35 U.S.C. 154(b) by 129 days.

(21) Appl. No.: 10/276,488

(22) PCT Filed: May 9, 2001

(86) PCT No.: PCT/EP01/05235

§ 371 (c)(1),
(2), (4) Date: Nov. 15, 2002

(87) PCT Pub. No.: WO01/94329

PCT Pub. Date: Dec. 13, 2001

(65) Prior Publication Data

US 2003/0171601 A1 Sep. 11, 2003

(30) Foreign Application Priority Data

Jun. 6, 2000 (AT) .......................................... A 983/2000

(51) Int. Cl.$^7$ ............................................. C07D 307/83
(52) U.S. Cl. ....................................... 549/307; 549/310
(58) Field of Search ................................. 549/307, 310

(56) References Cited

U.S. PATENT DOCUMENTS 5,616,733 A    4/1997    Vallejos et al. ............. 549/307
5,773,632 A    6/1998    Perrard et al. .............. 549/307

*Primary Examiner*—Ba K. Trinh
(74) *Attorney, Agent, or Firm*—Wenderoth, Lind & Ponach, LLP

(57) ABSTRACT

The invention relates to a method for the production of 2-coumarone or substituted 2-coumarones, whereby cyclohexanone or substituted cyclohexanone is reacted with a carboxyl-containing acylating agent a) to give methyl 2-(2-oxo-cyclohexyl)-2-hydroxyacetate or substituted methyl 2-(2-oxo-cyclohexyl)-2-hydroxyacetates, which are either $a_1$) directly converted to 2-coumarone or substituted 2-coumarones by means of catalytic gas-phase dehydrogenation, or $a_2$) dehydrated by means of azeotropic distillation under basic conditions, or by use of a strong acid, or a strongly acidic ion exchanger to a mixture of methyl 2-oxocyclohexylidenacetate and the enol-lactone of the 2-oxocyclohexylidenacetic acid, or a mixture of substituted methyl 2-oxocyclohexylidenacetate and the enol-lactone of the substituted 2-oxocyclohexylidenacetic acid, which is finally converted in turn by catalytic gas-phase dehydrogenation to 2-coumarone, or substituted 2-coumarones, or b) are directly converted under acidic or basic conditions into a mixture of methyl 2-oxocyclohexylidenacetate and the enol-lactone of 2-oxo-cyclohexylidenacetic acid, or a mixture of substituted methyl 2-oxocyclohexylidenacetate and the enol-lactone of the substituted 2-oxo-cyclohexylidenacetic acid, which is finally converted in turn by catalytic gas-phase dehydrogenation into 2-coumarone or substituted 2-coumarones.

10 Claims, No Drawings

METHOD FOR THE PRODUCTION OF 2-COUMARONE AND SUBSTITUTED 2-COUMARONES

2-Coumarone is an important raw material for synthesizing agrochemicals. The literature already discloses various processes for preparing 2-coumarone which is also referred to as 3H-2-benzofuran-2-one. They are based partly on multistage synthesis and partly on catalytic dehydrogenation in the gas phase. R. W. Layer et al. (U.S. Pat. No. 3,862,133) describe the synthesis for preparing γ-lactones of o-hydroxy-phenylacetic acid where the aromatic ring bears substituents. In the case of the use of phenyl and glyoxal, only very low yields of 2-coumarone are obtained, since the absence of substituents on the aromatic ring results in more than one reactive position and leads to many by-products.

According to the description of Pfitzer [sic] Inc. (GB 1 337 507), substituted 3H-2-benzofuran-2-ones are likewise prepared starting from substituted 2-methoxy-phenylacetic acid. The synthesis of 2-methylphenylacetic acid, subsequent ether cleavage and cyclization to 2-coumarone does not provide a cost-effective process.

Another method for preparing 5-chloro-3H-benzofuran-2-one is described by J. C. Vallejos et al (FR 2 686 880) starting from p-chlorophenol and glyoxylic acid in the presence of phosphinic acid and catalytic amounts of iodine or hydrochloric acid.

Although other methods for preparing 2-coumarone are mentioned in the literature, they have never reached the status of an industrial synthesis route: T. Fukagawa et al. report on the intramolecular acyloxylation of phenylacetic acid (J. Org. Chem., 1982, 47, 2491); E. Baciocchi et al. use trans-2,3-dichloro-2,3-dihydrobenzofuran as the reactant (J. Org. Chem., 1979, 44, 32) and H. E. Holmquist describes a synthesis starting from o-cresol and carbon monoxide.

Recently, J. C. Vallejos et al. (U.S. Pat. No. 5,616,733) described a process for preparing 2-coumarone by catalytic vapor phase dehydrogenation of the condensation product of cyclohexanone and aqueous glyoxylic acid which is initially dissolved in concentrated acetic acid. In addition to the rapid catalyst deactivation, the major disadvantages [sic] of this process is that only very small yields of 2-coumarone are obtained.

In a further reference, J. C. Vallejos et al. (U.S. Pat. No. 5,773,635) describe a possible increase in the yield of 2-coumarone by synthesis of the enol lactone of the condensation product of cyclohexanone and aqueous glyoxylic acid and subsequent catalytic gas phase dehydrogenation. The preparation of the condensation product from cyclohexanone and 50% aqueous glyoxylic acid disadvantageously requires the use of additional water and hydrochloric acid which, after the reaction is complete, have to be distilled off in addition to the excess of cyclohexanone. In a further synthesis step, the reaction mixture which comprises 2-oxocyclohexylideneacetic acid (cis and trans) and the enol lactone of 2-oxocyclohexylideneacetic acid is then enol-lactonized. After the vacuum distillation, the enol lactone of 2-oxocyclohexylideneacetic acid which has mainly formed is subjected to vapor phase dehydrogenation.

Unexpectedly, an improved process for preparing 2-coumarone and substituted 2-coumarones could be provided by catalytic gas phase dehydrogenation of the reaction products of cyclohexanone or substituted cyclohexanones and a carboxylic acylating agent in which not only the reaction products of cyclohexanone or substituted cyclohexanones and the carboxylic acylating agent, but also 2-coumarone and the substituted 2-coumarones are obtained in high yields.

The invention therefore provides a process for preparing 2-coumarone or substituted 2-coumarones, which is characterized in that cyclohexanone or substituted cyclohexanones are reacted with the carboxylic acylating agent a) to give 2-(2-oxocyclohexyl)-2-hydroxyacetate [sic] or substituted 2-(2-oxocyclohexyl)-2-hydroxyacetate [sic] which a₁) are either converted directly to 2-coumarone or substituted 2-coumarones by catalytic gas phase dehydrogenation, or a₂) dehydrated by azeotropic distillation under basic conditions or using a strong acid or a strongly acidic ion exchanger to give a mixture of methyl 2-oxocyclohexylideneacetate and the enol lactone of 2-oxocyclohexylideneacetic acid or a mixture of substituted methyl 2-oxocyclohexylideneacetate and the enol lactone of the substituted 2-oxocyclohexylideneacetic acid which is then in turn converted by catalytic gas phase dehydrogenation into 2-coumarone or substituted 2-coumarones, or b) reacted directly under acidic or basic conditions to give a mixture of methyl 2-oxocyclohexylideneacetate and the enol lactone of 2-oxocyclohexylideneacetic acid or a mixture of substituted methyl 2-oxocyclohexylideneacetate and the enol lactone of the substituted 2-oxocyclohexylideneacetic acid which is then in turn converted by catalytic gas phase dehydrogenation to 2-coumarone or substituted 2-coumarones.

The process according to the invention starts from cyclohexanone or substituted cyclohexanones of the formula (I)

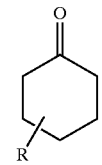

where R is H or a $C_1$–$C_3$-alkyl or alkoxy radical, and a carboxylic acylating agent of the general formulae (IIa) or (IIb)

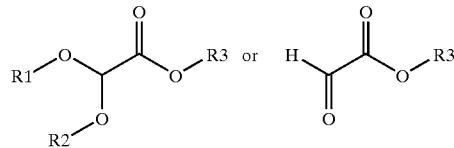

where, in the case of 2-coumarone preparation, R1, R2 and R3 may each independently be a methyl, ethyl or propyl radical, or R1 and R2 may each be a hydrogen atom and R3 a methyl, ethyl or propyl group and, in the case of substituted coumarone preparation, R3 may also be a hydrogen atom.

Examples of compounds of the formulae IIa and IIb are glyoxylic acid, methyl glyoxylate, ethyl glyoxylate, the methyl hemiacetal of methyl glyoxylate, the dimethyl acetal of methyl glyoxylate and the ethyl hemiacetal of ethyl glyoxylate. The carboxylic acylating agent may also be a mixture of compounds of the formula IIa and/or the formula IIb.

The course of the reaction can be seen from the following formula scheme—R is methyl, ethyl, propyl, methoxy, ethoxy or H:

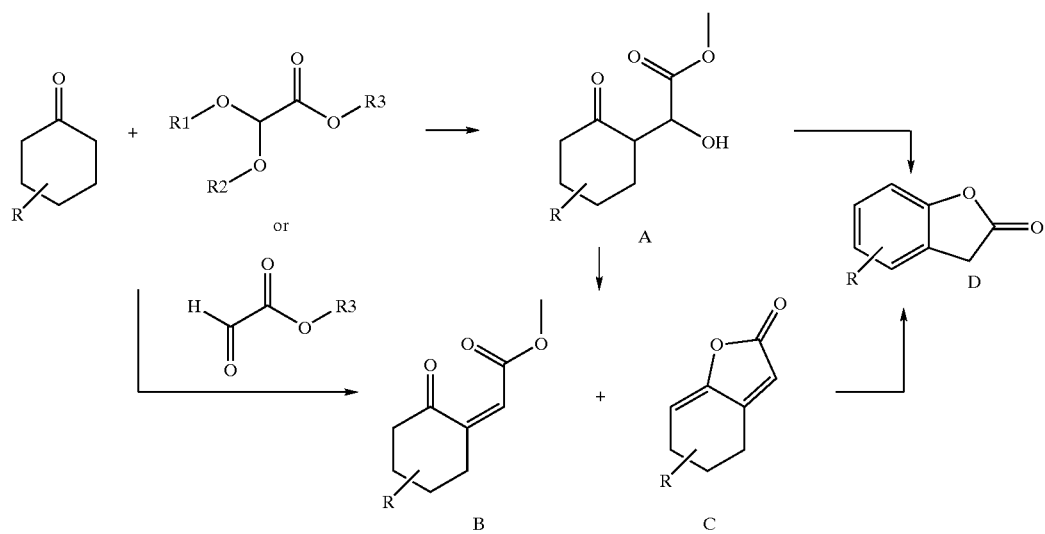

According to the invention, the reaction product A, methyl 2-(2-oxocyclohexyl)-2-hydroxyacetate or substituted methyl 2-(2-oxocyclohexyl)-2-hydroxyacetate, is obtained virtually quantitatively by reaction of cyclohexanone or substituted cyclohexanones with the carboxylic acylating agent under an inert atmosphere by preferably gradually metering the carboxylic acylating agent into cyclohexanone or the substituted cyclohexanone and removing the resulting alcohol (methanol, ethanol or propanol) from the reaction mixture overhead. The molar ratio of cyclohexanone or the substituted cyclohexanone to the carboxylic acylating agent is selected to be from 100:1 to 0.5:1. The molar ratio of cyclohexanone or the substituted cyclohexanone to the carboxylic acylating agent is preferably from 20:1 to 1:1, more preferably from 10:1 to 1.5:1. The temperature of the reaction mixture is from 50 to 190° C., preferably from 80 to 150° C. and more preferably from 95 to 145° C. The end of the reaction is detected by the depletion of the carboxylic acylating agent using a suitable in-process control. On completion of the reaction, excess cyclohexanone or substituted cyclohexanone is removed from the reaction mixture under reduced pressure. The reaction product A may optionally be distilled under vacuum, preferably at a vacuum of <0.5 mbar. The reaction product methyl 2-(2-oxocyclohexyl)-2-hydroxyacetate (=reaction product A) is in fact disclosed by the literature and has hitherto been obtained either by enzymatic reduction of the corresponding 2-oxoester (A. Schummer et al, Tetrahedron, Vol. 47, 1991, page 9019; S. Tsuboi et al, J. Org. Chem., 1987, 52, 1359; S. Tsuboi et al, Tetrahedron Letters, Vol. 27, 1986, page 1915), or by reaction of cyclohexanone, secondary amine and glyoxylic acid in a type of Mannich reaction and subsequent esterification (J. Schreiber et al, Bull. Soc. Chim. Fr., 1973, 2, page 625). However, preparation in a single synthesis step from inexpensive raw materials was hitherto unknown and is therefore a further part of the subject matter of the present invention.

In step $a_2$) of the process according to the invention, the reaction product A is dehydrated by water removal after the addition of an organic solvent and optionally of an acid or an acidic ion exchanger to give a mixture of methyl 2-oxocyclohexylideneacetate (reaction product B, cis or trans form) and the enol lactone of 2-oxocyclohexylideneacetic acid (reaction product C) or a mixture of substituted methyl 2-oxocyclohexylideneacetate (reaction product B, cis or trans form) and the substituted enol lactone of 2-oxocyclohexylideneacetic acid (reaction product C). The ratio of B to C may be controlled by the way the reaction is conducted, but also by metering in water. The reaction temperature is more than 50° C., more preferably from 80 to 160° C. Useful acids are in particular those which are soluble in an organic medium, and preference is given to using p-toluenesulfonic acid, methanesulfonic acid, concentrated sulfuric acid, etc., but even greater preference is given to using a strongly acidic ion exchanger. Useful organic solvents are preferably aliphatic or aromatic, optionally halogenated hydrocarbons such as benzene, toluene, xylenes and carbon tetrachloride, but also other organic solvents which, according to classical literature, serve to remove water.

The literature discloses the synthesis of the unsubstituted reaction products B and C by a preparation route which is different to the variant according to the invention but economically inefficient: A. Mondon et al, Chem. Ber., 96, 826, 1963; K. W. Rosenmund et al, Arch. Pharmarz. Ber. dtsch. pharmaz. Ges, 287, 441; A. W. Noltes et al, Rec. Trav. Chim., 80, 1334, 1961; Y. Arbuzov et al, Zhur. Obschch. Khim., 32, 3676, 1962, M. N. Kolosov et al, Zhur. Obschch. Khim., 32, 2983, 1962; F. Bonadies et al, Gazz. Chim. Ital., 113, 421, 1983.

According to the invention, the mixture of the reaction products B and C may also be obtained in a single synthesis step (step b) by reaction of cyclohexanone or substituted cyclohexanone with the carboxylic acylating agent under acidic or basic, but preferably acidic, conditions and under a protective gas atmosphere, preferably by gradually metering the carboxylic acylating agent into cyclohexanone or the substituted cyclohexanone, optionally in combination with an organic solvent. The alcohol (methanol, ethanol, propanol) formed in the reaction mixture may be distilled off overhead. The molar ratio of cyclohexanone or substituted cyclohexanone to the carboxylic acylating agent is chosen to be from 100:1 to 0.5:1. The molar ratio is preferably from 20:1 to 1:1, more preferably from 10:1 to 1.5:1. Useful organic solvents are more preferably aliphatic or aromatic, optionally halogenated hydrocarbons such as benzene, toluene, xylenes, carbon tetrachloride, etc., but also alcohols such as methanol, ethanol, etc. When an organic solvent is added, the volume ratio of organic solvent to cyclohexanone or the substituted cyclohexanone is from 100:1 to 0.2:1, preferably from 50:1 to 0.5:1 and more preferably from 10:1 to 1:1.

Useful acids are both inorganic and organic acids which may be used in an equimolar amount or in a molar excess or deficiency based on the carboxylic acylating agent. Preference is given in particular to hydrochloric acid, sulfuric acid, phosphoric acid, p-toluenesulfonic acid, methanesulfonic acid, etc. Particular preference is given to using a strongly acidic ion exchanger. The temperature of the reaction mixture is from 50 to 180° C., preferably from 80 to 150° C. and more preferably from 120 to 135° C. The end of the reaction is detected by the depletion of the carboxylic acylating agent using suitable in-process control.

On completion of the reaction, excess cyclohexanone or excess substituted cyclohexanone and, if required, also the organic solvent are removed from the reaction mixture under reduced pressure. The mixture of the reaction products B and C may optionally be distilled under vacuum, preferably at a vacuum of <500 mbar.

The process according to the invention is further characterized in that either the reaction product A or the mixture of reaction products B and C, either as the crude product or isolated, optionally in combination with methanol, ethanol or diethyl ether, is evaporated with the aid of a carrier gas and catalytically dehydrogenated using dehydrogenation catalysts which correspond to the prior art for aromatizing cyclic hydrocarbons and are disclosed, for example, by J. Wiley Interscience, New York, 1985; Houben-Weyl, Phenole, Vol.2, Georg Thieme-Stuttgart, 1976, 701-716 and J. H. Sinfelt in J. R. Anderson, M. Boudart: Catalysis Science and Technology, Vol. 1, Springer-Verlag, New York 1981 etc.

When methanol, ethanol or diethyl ether are added, the molar ratio of the reaction product A or the mixture of the reaction products B and C to methanol, ethanol or diethyl ether may be chosen to be from 1:0.2 to 100:0.2, and preference is given to a molar ratio of from 1:1 to 20:1. Particular preference is given to a molar ratio of from 2:1 to 10:1.

The catalytic gas phase dehydrogenation is effected at a temperature greater than 140° C., preferably at a temperature of from 200 to 300° C. and more preferably at a temperature of from 220 to 270° C. The catalyst used is preferably palladium or platinum on a solid support, for example aluminum oxide which preferably has a specific surface area of more than 1 m$^2$/g, in a concentration of from 0.5 to 6%.

On completed dehydrogenation, the condensate collected in cooling traps is distilled in order to isolate 2-coumarone or substituted 2-coumarones in high yields in pure form.

The process according to the invention is accordingly suitable for preparing reaction products from cyclohexanone or substituted cyclohexanones and a carboxylic acylating agent in high yields of above 90% which are subsequently catalytically dehydrogenated in the vapor phase to give 2-coumarone or substituted 2-coumarones in high yields of over 70%.

Compared to the prior art, the process according to the invention provides liquid, stable intermediates (reaction products A, B and C) in a very simple manner from inexpensive raw materials in a single synthesis step which can be directly converted to 2-coumarone or substituted 2-coumarones by catalytic gas phase dehydrogenation.

EXAMPLE 1

196 g (2 mol) of cyclohexanone were initially charged in a jacketed reactor and heated to 125° C. Over a period of 60 minutes, 120 g (1 mol) of the methyl hemiacetal of methyl glyoxylate were introduced and the methanol formed was removed from the reaction mixture using a nitrogen stream. After a further 30 minutes of reaction time, excess cyclohexanone and small amounts of methanol were removed from the reaction mixture at 105° C. under reduced pressure.

The virtually quantitative conversion provided the reaction product A in a 98% yield with a purity of 98% (GC+HPLC).

EXAMPLE 2

62 g (0.33 mol) of reaction product A were admixed with 300 ml of toluene and 6 g of ion exchanger Amberlyst 15 (Aldrich). After 60 minutes, the azeotropic distillation was ended and the ion exchanger filtered off. Excess toluene was removed from the reaction mixture under reduced pressure and, if required, the reaction mixture was distilled (boiling point: 90° C. at 1 mbar).

Quantitative conversion provided a mixture of reaction products B (cis form) and C which, according to the HPLC chromatogram, was composed of 95% of reaction product B and 4% of reaction product C.

EXAMPLE 3

196 g (2 mol) of cyclohexanone and 30 ml of concentrated hydrochloric acid were initially charged in a jacketed reactor and heated to 100° C. Over a period of 60 minutes, 120 g (1 mol) of the methyl hemiacetal of methyl glyoxylate [lacuna] were introduced and the reaction mixture was then boiled at 100° C. for a further 30 minutes. Excess cyclohexanone, methanol, water and hydrochloric acid were distilled off under reduced pressure. According to HPLC, the mixture of the reaction products was composed of 68% of reaction product C, 28% of reaction product B (cis form) and 3% of cis-2-oxocyclohexylideneacetic acid. The reaction mixture was distilled by distillation at a boiling point of 90° C. and a pressure of 1 mbar. Yield: 94% of the mixture of reaction products B and C based on the methyl hemiacetal of methyl glyoxylate.

EXAMPLE 4

56.1 g (0.5 mol) of 4-methylcyclohexanone and 18 g of a mixture of methyl glyoxylate and the methyl hemiacetal of methyl glyoxylate (about 80:20 after distillation) were initially charged in a jacketed reactor and continuously heated to 135° C. The methanol formed was discharged from the reaction mixture under atmospheric pressure. After a further 30 minutes of reaction time, excess 4-methylcyclohexanone and small amounts of methanol were removed from the reaction mixture at 100° C. under reduced pressure.

Virtually quantitative conversion provided methyl 2-(2-oxo-5-methylcyclohexyl)-2-hydroxyacetate in high yield with a purity of 95% (GC).

EXAMPLE 5

128.5 g (1 mol) of 4-methoxycyclohexanone and 29 g (0.333 mol) of methyl glyoxylate (freshly distilled) were initially charged in a jacketed reactor and continuously heated to 135° C. After a reaction time of 1.5 hours, excess 4-methoxycyclohexanone and small amounts of methanol were removed from the reaction mixture at 130° C. under reduced pressure.

Virtually quantitative conversion provided methyl 2-(2-oxo-5-methoxycyclohexyl)-2-hydroxyacetate in 95% yield with a purity of 92% (GC).

EXAMPLE 6

The products from Examples 1 to 3 were each diluted with methanol in a molar ratio of 4 to 1 (the mixture of reaction products from Example 2 also without methanol) and evaporated at a flow rate of 15 ml/h of nitrogen stream in an evaporator which, depending on the product, was maintained at a temperature of from 210 to 270° C. This vapor stream was passed into the reactor nitrogen stream at a flow rate of from 200 to 300 ml/h. The vertically arranged crude reactor which was filled with 1% of $Pd/Al_2O_3$ catalyst was operated at a temperature of 260° C. At the end of the reactor, the gas stream was passed through a plurality of cooling traps and the crude product was condensed in an acetonitrile-filled trap. The acetonitrile solution was subsequently analyzed by means of GC and HPLC. Based on the amount of reactant used from Examples 1 to 3, yields of greater than 70% were achieved. Increasing the gas stream even allowed yields of about 80% to be achieved. If required, 2-coumarone or the substituted 2-coumarones were distilled under reduced pressure to give a purity of 2-coumarone or substituted 2-coumarones of 99.8% (GC+HPLC).

What is claimed is:

1. A process for preparing 2-coumarone or substituted 2-coumarones, characterized in is that cyclohexanone or substituted cyclohexanones of the formula I

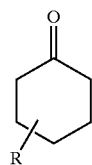

where R is H or a $C_1$–$C_3$-alkyl or alkoxy radical, are reacted with a carboxylic acylating agent of the general formula II

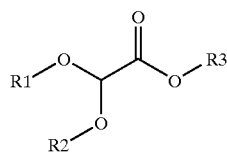

where R1 and R2 are each independently hydrogen or a $C_1$–$C_3$-alkyl radical and R3 is a $C_1$–$C_3$-alkyl radical,
   a) to give methyl 2-(2-oxocyclohexyl)-2-hydroxyacetate or substituted methyl 2-(2-oxocyclohexyl)-2-hydroxyacetates which
   $a_1$) are either converted directly to 2-coumarone or substituted 2-coumarones by catalytic gas phase dehydrogenation, or
   $a_2$) dehydrated by azeotropic distillation under basic conditions or using a strong acid or a strongly acidic ion exchanger to give a mixture of methyl 2-oxocyclohexylideneacetate and the enol lactone of 2-oxocyclohexylideneacetic acid or a mixture of substituted methyl 2-oxocyclohexylideneacetate and the enol lactone of the substituted 2-oxocyclohexylideneacetic acid which is then in turn converted by catalytic gas phase dehydrogenation into 2-coumarone or substituted 2-coumarones, or
   b) reacted directly under acidic or basic conditions to give a mixture of methyl 2-oxocyclohexylideneacetate and the enol lactone of 2-oxocyclohexylideneacetic acid or a mixture of substituted methyl 2-oxocyclohexylideneacetate and the enol lactone of the substituted 2-oxocyclohexylideneacetic acid which is then in turn converted by catalytic gas phase dehydrogenation to 2-coumarone or substituted 2-coumarones.

2. The process as claimed in claim 1, characterized in that the molar ratio in step a) or b) of cyclohexanone or substituted cyclohexanones to the carboxylic acylating agent is from 100:1 to 0.5:1.

3. The process as claimed in claim 1, characterized in that the reaction temperature in step a) or b) is above 50° C.

4. The process as claimed in claim 1, characterized in that the acids used in step $a_2$) or b) are inorganic or organic acids or an acidic ion exchanger.

5. The process as claimed in claim 4, characterized in that the acids used are p-toluenesulfonic acid, methanesulfonic acid, hydrochloric acid, sulfuric acid or a highly acidic ion exchanger.

6. The process as claimed in claim 1, characterized in that aliphatic or aromatic, optionally halogenated organic solvents are used in step $a_2$) for azeotropic distillation and optionally in step b) for diluting the reaction mixture during the reaction.

7. The process as claimed in claim 1, characterized in that the gas phase dehydrogenation in step $a_1$), $a_2$) and b) may be carried out using either the appropriate crude intermediates or else purified intermediates.

8. The process as claimed in claim 1, characterized in that the vapor phase dehydrogenation is performed at a temperature above 140° C.

9. The process as claimed in claim 1, characterized in that the gas phase dehydrogenation is carried out using a catalyst comprising palladium or platinum which is applied to an inert, solid support having a specific surface area of more than 1 $m^2/g$.

10. A process for preparing methyl 2-(2-oxocyclohexyl)-2-hydroxyacetate or substituted methyl 2-(2-oxocyclohexyl)-2-hydroxyacetates, characterized in that cyclohexanone or substituted cyclohexanones are reacted with the carboxylic acylating agent, whereupon the methyl 2-(2-oxocyclohexyl)-2-hydroxyacetate or substituted methyl 2-(2-oxocyclohexyl)-2-hydroxyacetates are optionally further processed as claimed in claim 1, $a_1$) or $a_2$) to give 2-coumarone or substituted 2-coumarone.

* * * * *